(12) United States Patent
Scheuermann et al.

(10) Patent No.: US 9,393,147 B2
(45) Date of Patent: Jul. 19, 2016

(54) KNEE BANDAGE HAVING A CORRECTIVE STRAP

(75) Inventors: Rainer Scheuermann, Raisdorf (DE); Hans B. Bauerfeind, Zeulenroda-Triebes (DE); Heinrich Hess, Kleinblittersdorf (DE)

(73) Assignee: Bauerfeind AG, Zeulenroda-Triebes (DE)

( * ) Notice: Subject to any disclaimer, the term of this patent is extended or adjusted under 35 U.S.C. 154(b) by 441 days.

(21) Appl. No.: 13/808,749

(22) PCT Filed: Jul. 8, 2011

(86) PCT No.: PCT/EP2011/003408
§ 371 (c)(1),
(2), (4) Date: Jan. 7, 2013

(87) PCT Pub. No.: WO2012/003992
PCT Pub. Date: Jan. 12, 2012

(65) Prior Publication Data
US 2013/0110023 A1   May 2, 2013

(30) Foreign Application Priority Data

Jul. 9, 2010  (DE) .......................... 10 2010 026 680

(51) Int. Cl.
*A61F 5/01* (2006.01)
*A61F 13/06* (2006.01)

(52) U.S. Cl.
CPC ............. *A61F 5/0123* (2013.01); *A61F 5/0109* (2013.01); *A61F 13/061* (2013.01); *A61F 2005/0176* (2013.01)

(58) Field of Classification Search
CPC ... A61F 5/0123; A61F 13/061; A61F 5/0109; A61F 2005/0176
USPC ............................. 602/26, 23, 5, 1; D24/190
See application file for complete search history.

(56) References Cited

U.S. PATENT DOCUMENTS

| 4,296,744 | A | * | 10/1981 | Palumbo | 602/26 |
| 4,765,318 | A | * | 8/1988 | Tranberg et al. | 602/26 |
| 5,277,697 | A | * | 1/1994 | France et al. | 602/16 |
| 5,613,943 | A | * | 3/1997 | Palumbo | 602/62 |

(Continued)

FOREIGN PATENT DOCUMENTS

| DE | 8115670 | 8/1981 |
| DE | 3838576 | 5/1991 |

(Continued)

OTHER PUBLICATIONS

International Search Report dated Nov. 23, 2011 in related International Application No. PCT/EP2011/003408, 3 pages.

(Continued)

*Primary Examiner* — Nicholas Woodall
*Assistant Examiner* — Tarla Patel
(74) *Attorney, Agent, or Firm* — Kilpatrick Townsend & Stockton LLP

(57) ABSTRACT

Disclosed is a bandage for knee joints that includes an elastic textile stocking, an annular or clasp-like elastic profiled insert arranged in or at the textile stocking to encase at least the lateral (fibula-side) section of the patella of the knee joint and at least one flexible, inelastic tensile strap essentially extending in the longitudinal direction of the bandage over the knee joint.

17 Claims, 4 Drawing Sheets

(56) References Cited

U.S. PATENT DOCUMENTS

| | | |
|---|---|---|
| 6,287,269 B1 | 9/2001 | Osti et al. |
| 6,551,264 B1* | 4/2003 | Cawley et al. .................. 602/16 |
| 8,845,567 B2* | 9/2014 | Herresthal ..................... 602/26 |
| 2004/0153017 A1* | 8/2004 | Simmons et al. ............... 602/26 |
| 2009/0156973 A1* | 6/2009 | Scott .............................. 602/26 |
| 2011/0004135 A1* | 1/2011 | Kausek .......................... 602/16 |

FOREIGN PATENT DOCUMENTS

| | | |
|---|---|---|
| DE | 3991334 | 5/1995 |
| DE | 102004040793 | 3/2006 |
| DE | 102006061060 | 6/2008 |
| DE | 102008029825 | 12/2009 |
| DE | 102009037823 | 2/2011 |
| FR | 2807644 | 10/2001 |
| WO | 2005087149 | 11/2005 |

OTHER PUBLICATIONS

International Preliminary Report on Patentability dated Jan. 15, 2013 in related International Application No. PCT/EP2011/003408, 7 pages.

* cited by examiner

KNEE BANDAGE HAVING A CORRECTIVE STRAP

CROSS REFERENCE TO RELATED APPLICATIONS

This application is the U.S. national phase of International Application No. PCT/EP2011/003408 filed on Jul. 8, 2011 as International Publication No. WO 2012/003992, which application claims priority to German Application No. 102010026680.9 filed on Jul. 9, 2010, the contents of both of which are incorporated herein by reference in their entireties.

FIELD OF THE INVENTION

The description relates to an improved knee joint bandage comprising correction straps to stabilize the kneecap (patella).

BACKGROUND

Knee joint bandages are described in DE 38 38 576 A1 and DE 10 2004 040 793 A1.

In such knee joint bandages, it is particularly disadvantageous that the medially centering effect of the strap is insufficient in many applications. In certain motions and/or in certain kinds of damage of the knee joint to be treated, the effect of the correction strap upon the patella is embodied too weakly so that no beneficial preventive or therapeutic effect occurs. Additionally, under certain other conditions of motion, for example when sitting with a bended knee, frequently pressure is applied upon the patella that is experienced as too strong and potentially disadvantageous for the therapy. Accordingly, it is desirable to provide a knee bandage of the above-mentioned type which avoids these disadvantages.

SUMMARY

According to the invention the correction strap is adjustable with regard to its effect upon the kneecap.

The knee joint bandage provided here primarily serves to correct the position of the kneecap by a targeted, adjustable mechanical impact of force. Knee joint bandages comprising an elastic textile material for the stabilization of the knee joint are known, which are pulled like a stocking over the knee joint. Frequently such bandages show a recess comprising a profiled insert (pelotte), which is arranged at or in the textile material. In connection with the force generated by the elasticity of the textile bandage upon the knee joint, the profiled insert primarily serves to mechanically stabilize the knee joint, drain tissue water present due to inflammatory events, and/or to ensure the physiologically correct position of the patella at the knee joint, depending on the bending status of the knee. This serves for the therapy of damaged knee joints. The bandage can also be used to prevent further damage of the knee joint.

In order to improve the function of such knee joint bandages, they comprise for the stabilization of the position of the patella at least one bendable, non-elastic tension member in the form of a correction strap, which essentially connects sections of the kneecap poles at the fibula side (exterior side of the knee, lateral) arched around the kneecap such that in an increased distance of these sections (moving apart) in the context with the knee joint bending the distance of the arch of the correction strap from the patella is reduced so that it is medially shifted or pushed towards the center of the knee and/or fixed here in a physiologically correct position.

The invention is based on the technical problem to provide an elastic knee joint bandage in which the displacement force applied upon the patella by a correction strap arranged in the knee joint bandage can be adjusted beneficially to the respective therapeutic and prophylactic conditions to improve the therapeutic success.

DETAILED DESCRIPTION

Figure 1:
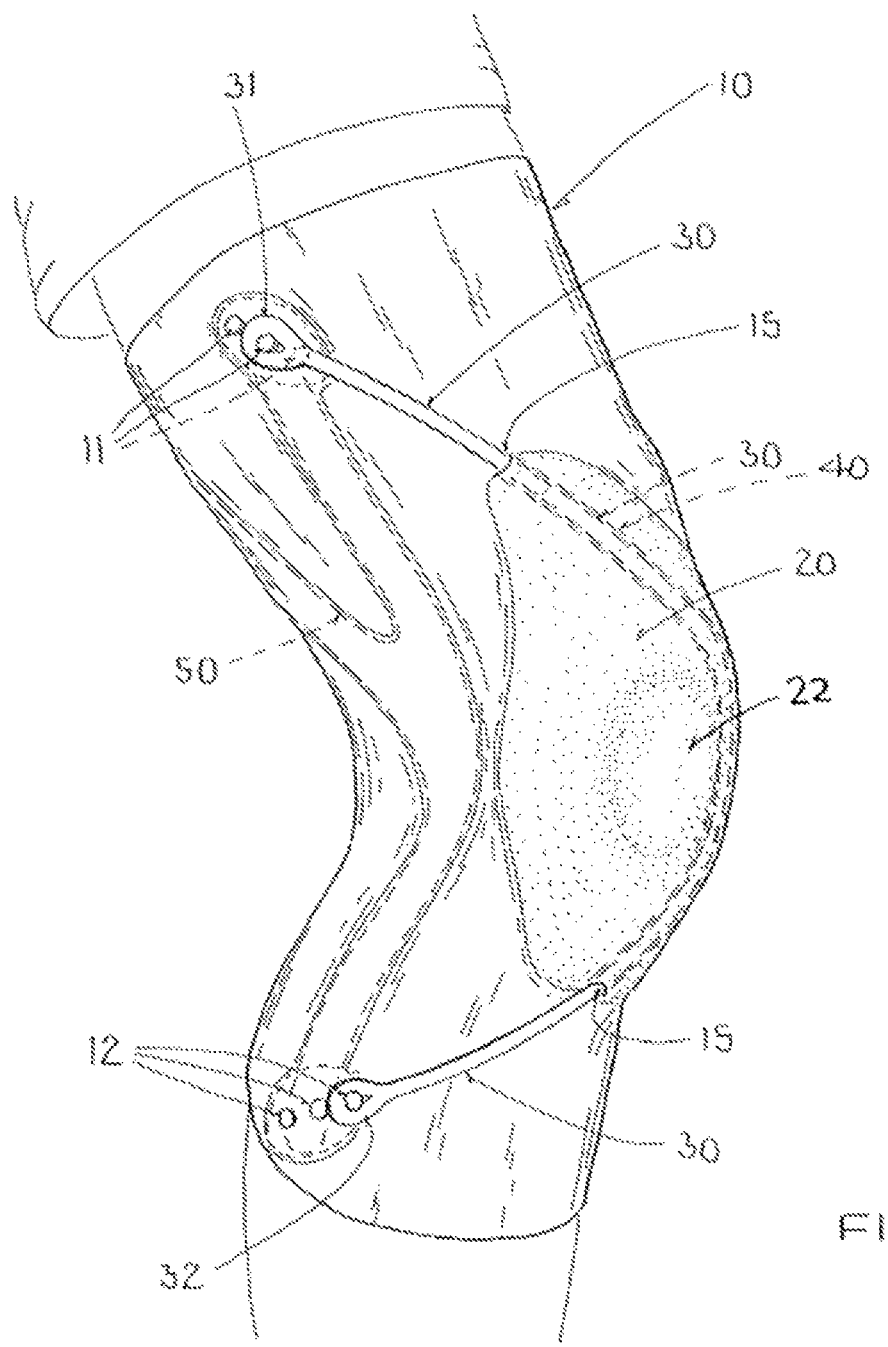
FIG. 1 shows a side view of a particular embodiment of the knee joint bandage according to the invention in a schematic illustration.

The invention completely attains the underlying technical problem in a bandage for a knee joint, which comprises an elastic textile stocking and an elastic profiled insert arranged in or at the textile stocking in an annular or clasp-like fashion, which encases at least the lateral section of the patella of the knee joint, i.e., at the fibula side, as well as at least one tensile strap, extending essentially in the longitudinal direction of the bandage over the knee joint, which is flexible but inelastic, which is guided laterally in or along the profiled insert. The tensile strap shows an upper end and a lower end, with at least one end being anchored by at least one upper and/or one lower anchoring point at the textile stocking in a detachable fashion, particularly in an adjustable fashion. In one section between the upper end and the lower end of the tensile strap it can apply a force upon the patella of the knee joint when the bandage is worn, which can displace the patella into its physiologically normal position and hold (fixate) it there.

If a tensile force is applied upon at least one end of the anchored tensile strap, which in a worn bandage is primarily generated when the knee is bent by the anchoring points moving apart, this acts upon the section as a force rector displacing or fixating the patella. Particularly in a damaged knee the fixing effect is based here in a dislocating force acting in the joint upon the patella being counteracted by an appropriately adjusted counterforce applied by the tensile strap, which counteracts the displacement of the patella.

The invention is primarily characterized in the effective length between the ends of the tensile strap being adjustable over an anchoring, not locally fixed or adjustable, of at least one end of the tensile strap in order to control the displacing or fixating force applied upon the patella. The force which the tensile strap can apply upon the patella depends on its effective length. This defines the effective length of the arch of the tensile strap which applies the force upon the patella when the ends connected at the anchoring points move apart when the knee is bent. A short effective length is equivalent to a stretched tensile strap when the bandage is used, which can apply a stronger force; a longer effective length is equivalent to a less stretched tensile strap during use, which applies a lesser force upon the patella.

The invention therefore provides to embody the tensile strap such that it can be altered in its effective length in order to allow predetermining the displacing or fixating effect of the tensile strap and thus the bandage upon the patella according to the respective disease, therapy approach, condition of motion, progression of therapy, therapy schedule, etc., in particular individually for each patient.

In a first embodiment of the bandage, at least the upper end of the tensile strap, i.e., the end pointing towards the torso, is fixated at different optional points at one of several distanced anchoring points. For example, several anchoring points, primarily arranged behind each other in the direction of extension of the tensile strap, can be alternatively connected in a detachable fashion in order to this way control the effective length of the tensile strap. In another variant of this embodiment, alternatively only the lower end of the tensile strap can be fixated respectively in a locally adjustable fashion. In another variant, both ends of the tensile strap can be fixated in a respectively locally adjustable fashion.

Preferably, the locally adjustable fixation is implemented via a detachable connection selected from hook and loop, buttons, and hook/eye systems. The detachable connection is not limited to these structures, though. One trained in the art knows additional detachable connections, which can be easily used particularly in the field of textile bandages.

It may be provided to mark the alternative anchoring points for an adjustable fixation of the tensile strap by coloring or using numbers or symbols so that, if applicable, the patient him/herself can simply perform the adjustment of the effective length of the tensile strap easily and reliably, upon prior instruction by the orthopedic physician or technician, for example depending on therapeutic requirements, predetermined therapy schedules, and/or present conditions of motion of the patient.

In another variant, the locally adjustable fixation of the tensile strap is also implemented by at least one coiling mechanism provided at or in the proximity of the anchoring points in order to adjust the effective length. Such a coiling mechanism may additionally be provided with a stopping mechanism latching against resistance, known per se. In another alternative embodiment a pulley mechanism, known per se, is provided at the anchoring points in order to additionally improve the ability for adjustment, particularly to ease the force required for such adjustments.

The invention provides that the tensile strap, although flexible, is embodied essentially inelastic. In the sense of the present invention, inelastic means primarily that the elasticity module of the tensile strap material and/or the internal structure of the tensile strap is considerably greater compared to the other elastic materials used in the bandage, particularly the textile web and the profiled insert, here particularly by one or more orders of ten. While preferred materials for a profiled insert are, for example, silicon elastomers with an average shore A-hardness, for example shore A 30 through 60, the tensile strap shall be produced, for example, in the form of a wire, rope, or web comprising a stiff material, such as steel or nylon. One trained in the art knows other, similar materials and structures, which in the sense of the invention are also suitable to implement the tensile strap used according to the invention; the invention also includes such additional materials and structures.

In a particular embodiment, the tensile strap is guided in a strong gliding channel arranged in or at the profiled insert. It may be connected fixed to the profiled insert and is particularly embodied such that the lateral forces applied via the tensile strap during use of the bandage cannot directly act upon the profiled insert, by which it could be destroyed, particularly since here during use friction forces, cutting like knives, develop between the tensile strap and the cushioning material of the profiled insert. Preferably the gliding channel is embodied in the form of a tube or groove, namely made from a mechanically tough and friction-resistant material, for example Teflon, nylon, allowing a low-friction gliding of the tensile strap while avoiding material abrasion.

In another embodiment, the guiding channel itself is also elastic. Here, the elasticity module of the material of the guiding channel is selected such that it matches the elasticity module of the profiled insert so that particularly shearing forces are avoided, which disturb the connection between the guiding channel and the profiled insert.

In an alternative embodiment the tensile strap is fixated locally fixed inside or at the profiled insert. This way, friction and cutting forces acting upon the cushioning material can be avoided; the cushioning material follows the motion of the tensile strap at the boundary between the tensile strap and the profiled insert. For example, the tensile strap may be cast into the material of the profiled insert. Alternatively, the tensile strap may be adhered or welded onto the profiled insert or the cushioning cover of the profiled insert. In a particular embodiment, the tensile strap is arranged such that it extends in the applied state between the profiled insert and the knee in order to essentially directly contact the patella to be corrected or fixated. For this purpose, for example, the tensile strap can extend directly at or within the cushioning cover arranged between the profiled insert and the patella. Preferably, the tensile strap is sewn or welded to said tensile strap. Alternatively or additionally, the tensile strap itself is covered directly with a cushioning material in order to avoid any mechanical skin irritation. This may be beneficial when alternatively the tensile strap extends outside along the profiled insert, preferably directly at the knee joint. For example, the tensile strap is formed from silicone coated nylon thread, forming a woven strap covered by silicon elastomer.

In another additional or alternative embodiment, the tensile strap is embodied interchangeable at the bandage. It may be embodied in alternative thicknesses, lengths, and/or degrees of elasticity for the use in the very same bandage. For example, it may be necessary in the very same bandage to one time use a stiffer and another time a more elastic tensile strap, depending on the condition of motion. This way, the effect of the tensile strap, in addition to the adjustment option of the ends of the tensile strap, can also be adjusted over a greater range in order to further improve the ability for adjustment of the function of the knee joint bandage.

In a particular embodiment, it is provided that the tensile strap extends in the area of the patella laterally at the inside, i.e., the interior area of the bandage facing the knee, and at least exits at a passage site of the bandage out of the interior of the textile stocking and then extends on the exterior of the bandage, thus the external area facing the knee, in order to here, preferably at the textile stocking itself, be anchored at least at one anchoring point. This way, advantageously the adjustment of the effective length is also possible when the bandage is worn. Additionally, it can be avoided here that it is necessary that the means embodying the detachable, locally variable connection according to the invention are arranged at the inside of the bandage, thus facing the body, which here may disadvantageously be connected to a local, mechanical irritation of the skin. However, the invention is not limited to externally located detachable connection means or an external progression of at least one end of the tensile strap.

In particular, it is provided that one end of the tensile strap is fastened locally fixed directly at or in the textile stocking in a non-detachable or adjustable fashion, while the other end is fastened adjustably according to the invention. For this purpose, the tensile strap is preferably sewn, glued, or welded to the textile stocking. In a preferred embodiment, the lower end of the tensile strap is welded or glued to the textile stocking and the upper end of the tensile strap is guided from the interior to the exterior of the bandage where it is easily accessible to the user and can be fixated at its end in an adjustable fashion.

In one embodiment of the bandage, it shows at least one stabilizing flat spring element at or in the textile stocking at the side of the bandage extending in the longitudinal extension of the bandage, in order to stabilize the knee joint bandage per se in a mechanical fashion. In a particular embodiment of such an embodiment, it is now provided that at least one of the anchoring points at the end of the tensile strap is directly connected to the flat spring element in a force-fitting fashion. This way a better local fixation of the tensile strap can be achieved, which improves the application of force upon the tensile strap by bending the knee and thus also the mechanic effect upon the patella.

The bandage helps to ease pain caused by a faulty positioning of the kneecap. Advantageously, the wear and tear of the knee joint cartilage located behind the kneecap can be prevented. The objective of the invention also comprises the medical, therapeutic, and/or prophylactic use of the bandage according to the invention for the prophylaxis, easing, and/or therapy of diseases of the joints in the animal or human body, particularly diseases of the knee joint, which are connected to an unhealthy displacement of the patella. This includes particularly patella lateralization, patella dysplasia, retro-patella arthritis, chondropathia patellae, acute patella syndrome, chondromalacia patellae, the status after patella luxation, as well as posttraumatic and postoperative conditions.

The invention is explained in greater detail in the figures and the corresponding description, without being limited thereto.

FIG. 1 shows a side view of a particular embodiment of the knee joint bandage according to the invention in a schematic illustration. Shown here is a top view of the inside of the knee joint. At a textile stocking 10, facing the inside, thus the knee joint, a profiled insert 20 is arranged encompassing the patella. The profiled insert centers at a window or a material reduction 22 over the patella. An inelastic flexible tensile strap 30, extending at least in the area of the profiled insert 20 inside the textile stocking 10, is guided along the profiled insert in a channel 40. The tensile strap 30 passes through the penetration 15 from the inside of the textile web to the outside in order to be fastened via the upper end 31 or the lower end 32 at variable anchoring points 11, 12. In a particular embodiment, the textile stocking additionally comprises a flat spring element 50. The anchoring points 11, 12 may be connected to the flat spring element 50 in a force-fitting fashion in order to mechanically stabilize the anchoring points.

Figure 2:
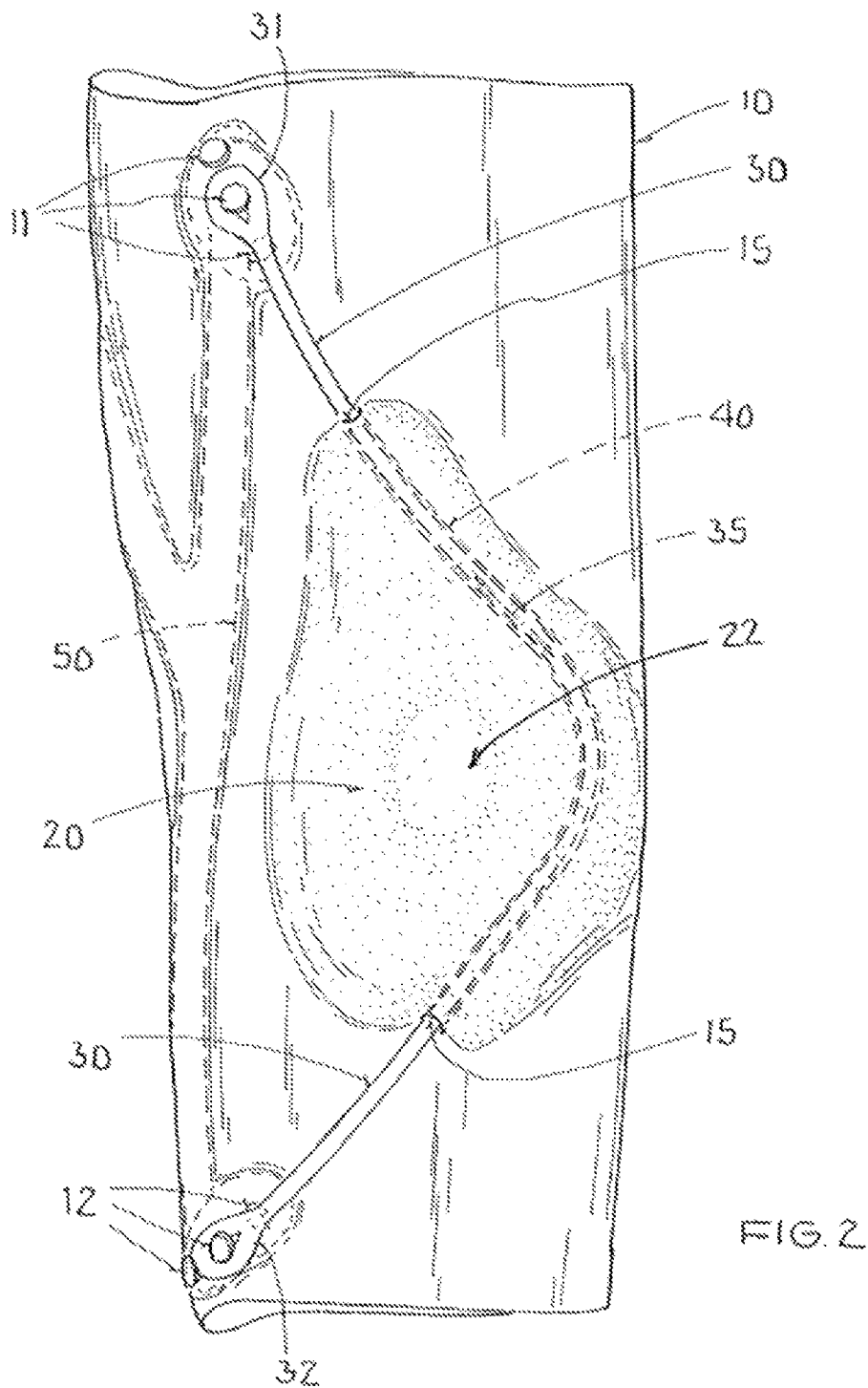
FIG. 2 shows a top view of the removed bandage according to FIG. 1.

FIG. 2 shows a top view of the removed bandage according to FIG. 1. The tensile strap 30 acts over the effective length 35 in a displacing or fixating fashion upon the patella, which is made to rest in the area of the window/recess 22 of the profiled insert 20 when the bandage is worn.

Figure 3:
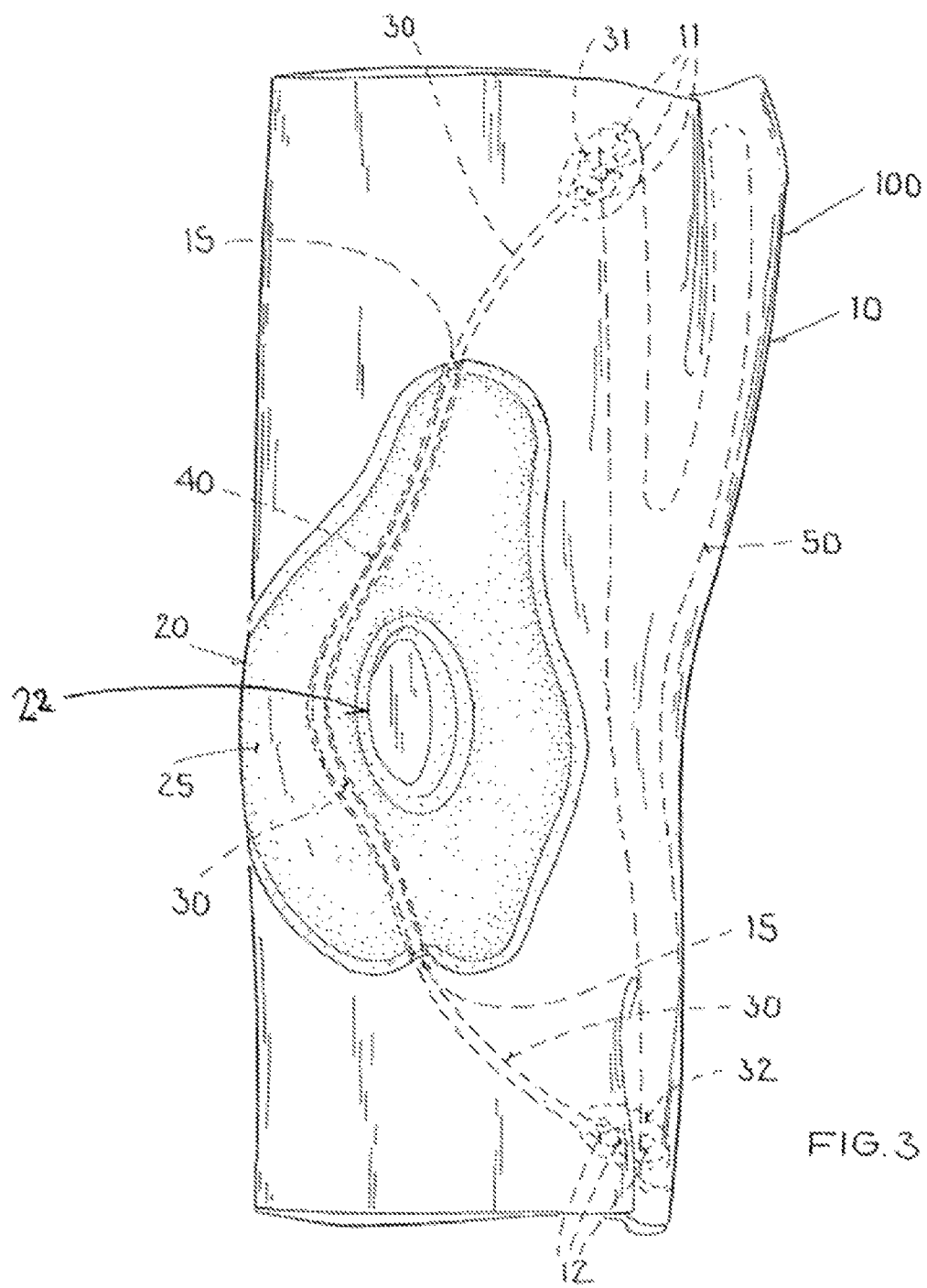
FIG. 3 shows an inside view of the removed bandage according to FIGS. 1 and 2.

FIG. 3 shows an inside view of the removed bandage according to FIGS. 1 and 2. The profiled insert 20 is connected to the textile stocking via the cushioning cover 25, which is welded or adhered at the external circumferential edge and in the area of the window/recess 22 of the textile material of the textile stocking 2. The tensile strap 30 is guided in a gliding channel 40 inside the profiled insert. The tensile strap exits at the penetrations 15 to the respective outside of the textile stocking.

Figure 4:
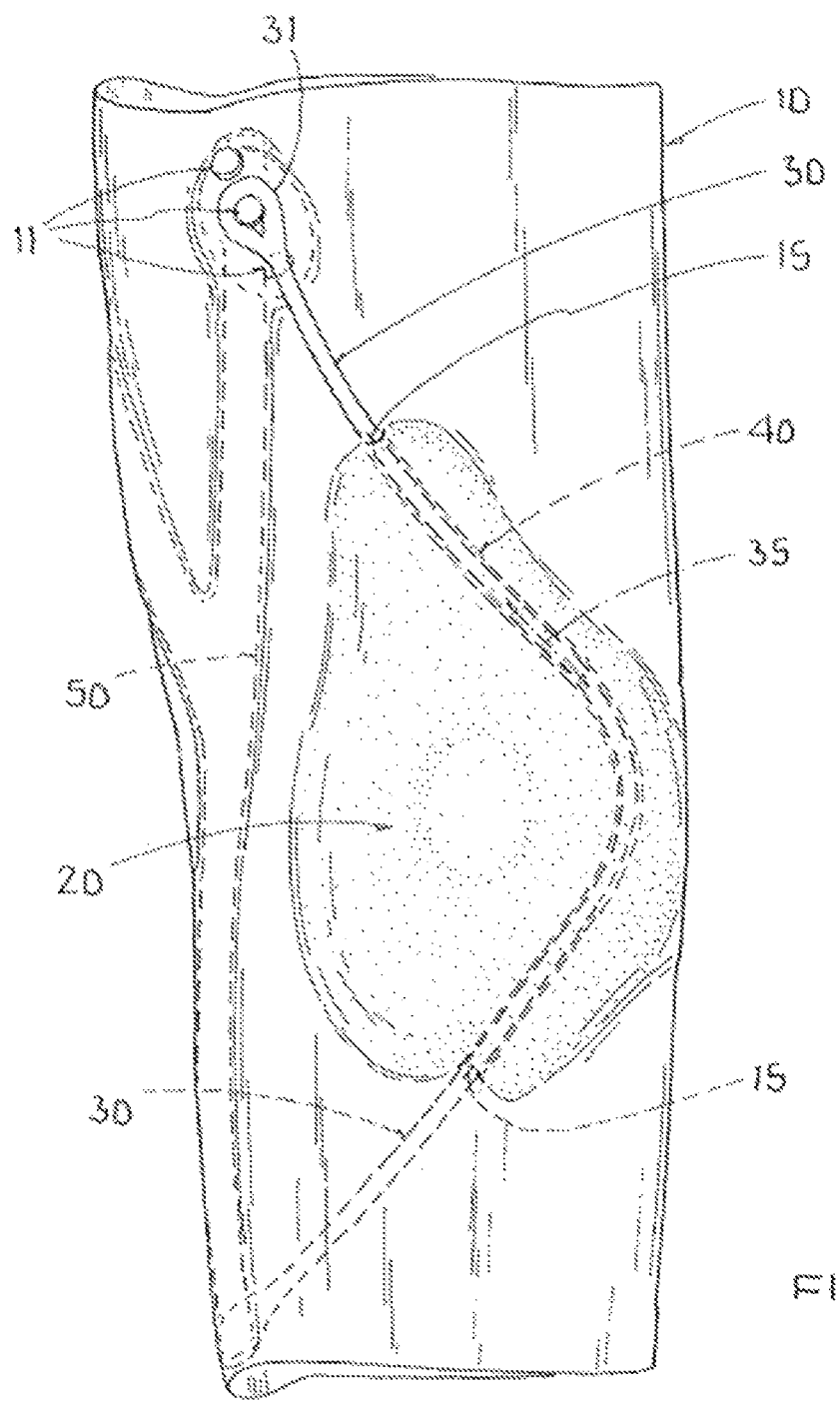
FIG. 4 shows an alternative embodiment of the bandage according to the invention.

FIG. 4 shows an alternative embodiment of the bandage according to the invention. The tensile strap 30 is locally fixed in the area of the lower end at or inside the textile strap. An optional adjustment results via the upper end 31 in connection with the variable connection points 11. A penetration 15 at the lower section of the tensile strap may be waived if the tensile strap is fastened at or in the inside of the textile stocking 10.

The invention claimed is:

1. A bandage for knee joints comprising:
an elastic textile tubular stocking,
an elastic profiled insert arranged in the elastic textile tubular stocking, wherein the elastic profiled insert comprises an annular window or material reduction that encompasses at least a lateral (fibula-side) section of a patella of a knee joint, and
at least one flexible, inelastic tensile strap that extends generally a longitudinal direction of the bandage around the knee joint and is guided laterally in the elastic profiled insert, wherein:
the longitudinal direction extends between a portion above the knee joint and a portion below the knee joint;
the elastic textile tubular stocking includes at least one upper anchoring point and at least one lower anchoring point;
the at least one flexible, inelastic tensile strap is a continuous single-piece extending from an upper end above the knee joint to a lower end below the knee joint;
the upper end of the at least one flexible, inelastic tensile strap is attached to the at least one upper anchoring point and, when the bandage is worn, the upper end is located above the knee joint on a first side of the patella;
the lower end of the at least one flexible, inelastic tensile strap is attached to the at least one lower anchoring point and, when the bandage is worn, is located below the knee joint on the first side of the patella;
when the bandage is worn, a central portion of the at least one flexible, inelastic tensile strap curves around a second side of the patella that is opposite the first side of the patella such that the at least one flexible, inelastic tensile strap applies a centering force to the patella due to the upper and lower anchoring points moving apart when the knee joint is bent;
an effective length of the at least one flexible, inelastic tensile strap is adjustable at one or both of the anchoring points in order to control the centering force applied by the at least one flexible, inelastic tensile strap;
the at least one flexible, inelastic tensile strap passes through at least one penetration to exit an inside of the elastic textile tubular stocking to its outside;
the at least one flexible, inelastic tensile strap extends inside a cushioning cover arranged between the elastic profiled insert and the patella; and
either the at least one flexible, inelastic tensile strap is guided in a gliding channel arranged within the elastic profiled insert or the at least one flexible, inelastic tensile strap is welded, adhered to, or sewn to the cushioning cover.

2. A bandage according to claim 1, wherein the effective length of the at least one flexible, inelastic tensile strap can be altered by a detachable connection that is adjustable at least at one of the anchoring points.

3. A bandage according to claim 2, with the detachable connection comprising at least one of hook and loop, knotting, or hook/eye systems.

4. A bandage according to claim 1, with at least one stabilizing flat spring element being arranged at the elastic textile tubular stocking at a side of the bandage extending in the longitudinal direction of the bandage, and at least one of the anchoring points of the at least one flexible, inelastic tensile strap being connected to the at least one stabilizing flat spring element in a force-fitting fashion.

5. A bandage according to claim 1, with the at least one flexible, inelastic tensile strap comprising a cushioning coating connected thereto in a fixed manner.

6. A bandage according to claim 5, with the cushioning coating being a coating with silicon elastomer.

7. A bandage according to claim 1, wherein the at least one flexible, inelastic tensile strap comprises an inelastic wire.

8. A bandage according to claim 7, wherein the inelastic wire comprises nylon or steel.

9. A bandage according to claim 1, wherein the central portion of the at least one flexible, inelastic tensile strap comprises a curved portion that is approximately parallel to an inner edge of the annular window or material reduction of the elastic profiled insert.

10. A bandage according to claim 1, wherein the at least one flexible, inelastic tensile strap, when viewed from a front side, forms an approximate right angle.

11. A bandage according to claim 10, wherein the at least one flexible, inelastic tensile strap, when viewed from a front side, forms a more acute angle as the knee joint bends.

12. A bandage for knee joints comprising:
an elastic stocking;
an elastic insert arranged in the elastic stocking, the elastic insert comprising an annular window or material reduction to encompass at least a lateral section of a patella of a knee joint; and
at least one flexible tensile strap that extends generally in a longitudinal direction of the bandage and is guided laterally in the elastic insert, wherein:
the longitudinal direction extends between a portion above the knee joint and a portion below the knee joint;
the at least one flexible tensile strap is a continuous single-piece extending from an upper end above the knee joint to a lower end below the knee joint;
the upper end of the at least one flexible tensile strap is attached to at least one upper anchoring point of the elastic stocking and, when the bandage is worn, is disposed above the knee joint on a first side of the patella;
the lower end of the at least one flexible tensile strap is attached to at least one lower anchoring point of the elastic stocking and, when the bandage is worn, is disposed below the knee joint on the first side of the patella;
when the bandage is worn, a central portion of the at least one flexible tensile strap curves around a second side of the patella that is opposite the first side of the patella to apply a centering force to the patella due to the upper and lower anchoring points moving apart when the knee joint is bent;
an effective length of the at least one flexible tensile strap is adjustable at one or both of the upper and lower anchoring points to control the centering force applied by the at least one flexible tensile strap;
the at least one flexible tensile strap extends inside a cushioning cover arranged between the elastic insert and the patella; and
the at least one flexible tensile strap is coupled with the elastic insert.

13. The bandage of claim 12, wherein the at least one flexible tensile strap is welded, adhered to, or sewn to the cushioning cover.

14. The bandage of claim 12, wherein the at least one flexible tensile strap is welded, adhered to or sewn to the cushioning cover only in an area adjacent to the patella.

15. The bandage of claim 12, wherein the at least one flexible tensile strap is guided in a gliding channel arranged in and passing through the elastic insert.

16. A bandage for knee joints comprising:
an elastic stocking;
an elastic insert arranged in the elastic stocking, the elastic insert comprising an annular window to encompass at least a lateral section of a patella of a knee joint; and
at least one flexible tensile strap that extends generally in a longitudinal direction of the bandage and is guided laterally in the elastic insert, wherein:
the longitudinal direction extends between a portion above the knee joint and a portion below the knee joint;
the at least one flexible tensile strap is a continuous single-piece extending from an upper end above the knee joint to a lower end below the knee joint;
the upper end of the at least one flexible tensile strap is attached to at least one upper anchoring point of the elastic stocking and, when the bandage is worn, is disposed above the knee joint on a first side of the patella;
the lower end of the at least one flexible tensile strap is attached to at least one lower anchoring point of the elastic stocking and, when the bandage is worn, is disposed below the knee joint on the first side of the patella;
when the bandage is worn, a central portion of the at least one flexible tensile strap curves around a second side of the patella that is opposite the first side of the patella to apply a centering force to the patella due to the upper and lower anchoring points moving apart when the knee joint is bent;
the central portion of the at least one flexible tensile strap comprises a curved portion that is approximately parallel to an inner edge of the annular window of the elastic insert; and
the at least one flexible tensile strap, when viewed from a front side, forms an approximate right angle.

17. The bandage for knee joints of claim 16, wherein the at least one flexible tensile strap is welded, adhered to, or sewn to a cushioning cover.

* * * * *